United States Patent
Zaragoza Doerwald et al.

(10) Patent No.: US 9,522,885 B1
(45) Date of Patent: Dec. 20, 2016

(54) METHOD FOR PREPARATION OF 6-TRIFLUOROMETHYLPYRIDINE-3-CARBOXYLIC ACID DERIVATIVES FROM TRIFLUOROACETYLACETIC ACID

(71) Applicant: Lonza Ltd, Visp (CH)

(72) Inventors: Florencio Zaragoza Doerwald, Visp (CH); Michael Bersier, Ausserberg (CH); Christoph Taeschler, Termen (CH)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 14/898,791

(22) PCT Filed: Jul. 17, 2014

(86) PCT No.: PCT/EP2014/065366
§ 371 (c)(1),
(2) Date: Dec. 16, 2015

(87) PCT Pub. No.: WO2015/007837
PCT Pub. Date: Jan. 22, 2015

Related U.S. Application Data

(60) Provisional application No. 61/856,262, filed on Jul. 19, 2013.

(30) Foreign Application Priority Data

Jul. 19, 2013 (EP) ..................................... 13177234
Dec. 4, 2013 (EP) ..................................... 13195611
Dec. 18, 2013 (EP) ..................................... 13198150

(51) Int. Cl.
*C07D 213/83* (2006.01)
*C07D 213/803* (2006.01)

(52) U.S. Cl.
CPC ................. *C07D 213/803* (2013.01)

(58) Field of Classification Search
CPC .................................................. C07D 213/83
See application file for complete search history.

(56) References Cited

U.S. PATENT DOCUMENTS

| | | |
|---|---|---|
| 6,534,445 B1 | 3/2003 | Edmunds et al. |
| 6,673,938 B1 | 1/2004 | Edmunds et al. |
| 7,858,621 B2 | 12/2010 | Kim et al. |
| 2006/0199964 A1 | 9/2006 | Jackson et al. |
| 2009/0137558 A1 | 5/2009 | Fisher et al. |
| 2014/0113898 A1 | 4/2014 | Pajouhesh et al. |

FOREIGN PATENT DOCUMENTS

| | | |
|---|---|---|
| WO | WO 00/39094 | 7/2000 |
| WO | 2004/078272 | * 9/2004 |
| WO | WO 2004/078729 | 9/2004 |
| WO | WO 2006/059103 | 6/2006 |
| WO | WO 2008/013414 | 1/2008 |
| WO | WO 2012/061926 | 5/2012 |

OTHER PUBLICATIONS

International Preliminary Report on Patentability for PCT/EP2014/065366, mailed Dec. 12, 2014.
International Search Report and Written Opinion for PCT/EP2014/065366, mailed Sep. 2, 2014.
E. Okada et al., "A Simple and Convenient Synthetic Method for Alpha-Trifluoromethylpyridines," Heterocycles.International Journal for Reviews and Communications in Heterocyclic Chemistry, Elsevier Science Publishers B.V. Amsterdam, NL, vol. 46, Jan. 1, 1997, pp. 129-132.
D. M. Volochnyuk et al., "Electron-rich amino heterocycles for regiospecific synthesis of trifluoromethyl containing fused pyridines," Synthesis, George Thieme Verlag, Stuttgart, Germany, vol. 10, Jul. 21, 2003, pp. 1531-1540.
R. W. Leiby, "Synthesis of 3-Amino-4(3H)-quinazolinones from N-(2-Carbomethoxyphenyl) Imidate Esters," J. Org. Chem., 1985, 50, pp. 2926-2929.
T. Moriguchi et al., "Addition-Elimination Reaction in the Trifluoroacetylation of Electron-Rich Olefins," J. Org. Chem., 1995, 60, pp. 3523-3528.
F. Swarts, "Trifluoroacetylacetic acid," Bulletin de la CLasse des Sciencies, Academie Royale de Belgique, 1926, 12, pp. 721-725.

* cited by examiner

*Primary Examiner* — D M Seaman
(74) *Attorney, Agent, or Firm* — Dority & Manning, P.A.

(57) ABSTRACT

The invention discloses a method for the preparation of 6-trifluoromethylpyridine-3-carboxylic acid derivatives (I) from trifluoroacetylacetic acid (II) and orthoesters (III), and their use for the preparation of pharmaceutical, chemical or agro-chemical products.

9 Claims, No Drawings

METHOD FOR PREPARATION OF 6-TRIFLUOROMETHYLPYRIDINE-3-CARBOXYLIC ACID DERIVATIVES FROM TRIFLUOROACETYLACETIC ACID

CROSS REFERENCE TO RELATED APPLICATIONS

This application is the U.S. National Stage entry of International Application Number PCT/EP2014/065366 filed under the Patent Cooperation Treaty and having a filing date of Jul. 17, 2014, which claims priority to European Patent Application No. 13198150.8 having a filing date of Dec. 18, 2013, European Patent Application No. 13195611.2 having a filing date of Dec. 4, 2013, European Patent Application No. 13177234.5 having a filing date of Jul. 19, 2013, and U.S. Provisional Patent Application No. 61/856,262 having a filing date of Jul. 19, 2013, all of which are hereby incorporated by reference herein in their entirety for all purposes.

FIELD OF THE INVENTION

The invention discloses a method for the preparation of 6-trifluoromethylpyridine-3-carboxylic acid derivatives from trifluoroacetylacetic acid and orthoesters, and their use for the preparation of pharmaceutical, chemical or agrochemical products.

BACKGROUND OF THE INVENTION

2-Trifluoromethylpyridines and 6-trifluoromethylpyridine-3-carboxylic acid derivatives are intermediates for the preparation of biologically active compounds. For instance, WO 00/39094 A1 discloses trifluoromethylpyridine as herbicides, WO 2006/059103 A2 discloses trifluoromethylpyridines as intermediates in the production of pharmaceutical, chemical and agro-chemical products, WO 2008/013414 A1 discloses trifluoromethylpyridines as vanilloid receptor antagonists and WO 2012/061926 A1 describes trifluoromethylpyridines as calcium channel blockers.

The common route for the preparation of 6-trifluoromethylpyridine-3-carboxylic acid derivatives was first reported by Okada et al., Heterocycles 1997, 46, 129-132, and has only been slightly modified by others. The common synthetic strategies are summarized in Scheme 1:

Scheme 1

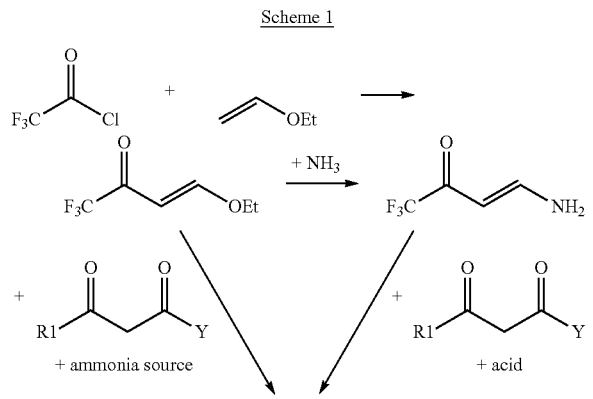

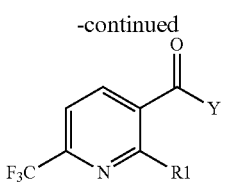

This route has disadvantages for the large scale production of 6-trifluoromethylpyridine-3-carboxylic acid derivatives, because ethylvinylether is highly flammable and therefore difficult to handle, and because the trifluoroacetylated enolether and the trifluoroacetylated enamine intermediates are unstable and cannot be stored for a longer time. Moreover, most vinyl ethers are mutagenic.

Volochnyuk et al., Synthesis 2003, 10, 1531-1540, discloses a method for the preparation of pyridines substituted in position 4 with a trifluoromethyl residue. The pyridines are part of a bicyclic heterocycle. The method starts with aminopyrazole, which is reacted with trifluoroacetylketones or with the ethyl ester of trifluoroacetylacetic acid. The method is principally not suited to prepare the desired 6-trifluoromethylpyridine-3-carboxylic acid derivatives of the instant invention, since position 6 in Volochnyuk is the endocyclic C atom connecting the pyrazol part with the pyridine part of the bicyclic heterocycle of Volochnuyk. The disclosure does not mention the use of trifluoroacetylacetic acid at all.

WO 2004/078729 A1 discloses the preparation of compound of formula (Xa) from inter alia 4-alkoxy-1,1,1-trifluorobut-3-en-2-ones, which are prepared from vinylethers;

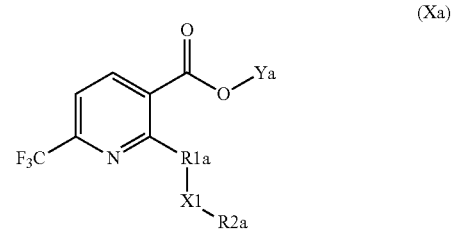

and discloses on page 18 in example P2 the use of 4-ethoxy-1,1,1-trifluorobut-3-en-2-one for the preparation of compound of formula (I-2).

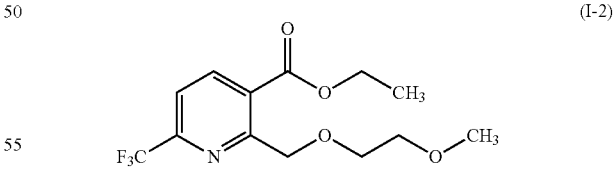

Compound of formula (Xa) and compound of formula (I-2) are intermediates for the preparation of herbicides.

F. Swarts, Bulletin de la Classe des Sciences, Academie Royale de Belgique, 1926, 12, 721-725 discloses the preparation of a certain substrate used in instant invention.

There was a need for an improved procedure for the preparation of 6-trifluoromethylpyridine-3-carboxylic acid derivatives.

This need was met by the method of instant invention as outlined below.

R. W. Leiby, J. Org. Chem. 1985, 50, 2926-2929, discloses the reaction of anthranilates with orthoesters, therefore it was expected that enamines, which are structurally comparable to anthranilates, react with orthoesters as well, and which then would no longer be available for a reaction with trifluoroacetylacetic acid to trifluoromethylpyridine.

Unexpectedly, in a mixture containing orthoesters, enamines and trifluoroacetylacetic acid, the formation of trifluoromethylpyridine was observed.

Compared to prior art, the method of the instant invention offers several advantages: Importantly, no vinyl ethers, trifluoroacetylated enolether intermediates or isolated trifluoroacetylated enamine intermediates are required, e.g. as is used in form of a 4-ethoxy-1,1,1-trifluorobut-3-en-2-one, named 1-ethoxy-3-oxo-4-trifluorobutene, in WO 2004/078729 A1, that is the substance (3) in example P2 of the WO 2004/078729 A1, which is prepared e.g. according to Moriguchi, J. Org. Chem., 1995, 60, 3523-3528 from vinylether, as cited in WO 2004/078729 A1 on page 16 lines 8-9. Moreover, the method of the present invention reduces the number of synthetic steps compared to known procedures, what reduces the overall costs.

In the following text, if not otherwise stated, the following meanings are used:
ambient pressure usually 1 bar, depending on the weather;
alkyl means a linear or branched alkyl, examples of alkyl include methyl, ethyl, n-propyl, isopropyl, n-butyl, sec-butyl, tert-butyl, pentyl, hexyl, heptyl and the like;
cyclic alkyl or cyclo alkyl include cyclo aliphatic, bicyclo aliphatic and tricycle aliphatic residues; examples of "cycloalkyl" include cyclopropyl, cyclobutyl, cyclopentyl, cyclohexyl, cycloheptyl, norbornyl and adamantyl;
alkoxy means alkyl-O, i.e. the radical obtained by removal of the oxygen-bound hydrogen from an aliphatic alcohol;
(alkoxy)alkoxy refers to alkoxy groups, in which the alkyl group is substituted with one additional alkoxy group; examples of (alkoxy)alkoxy include methoxymethoxy with formula MeO—$CH_2$—O—, 2-(methoxy)ethoxy with formula MeO—$CH_2$—$CH_2$—O— and 2-(cyclopropylmethoxy)ethoxy with formula $(C_3H_5)CH_2$—O—$CH_2$—$CH_2$—O—;
Ac acetyl;
tBu tertiary butyl;
cyanuric acid chloride 2,4,6-trichloro-1,3,5-triazine
DBU 1,8-diazabicyclo[5.4.0]undec-7-ene;
DABCO 1,4-diazabicyclo[2.2.2]octane;
DMF N,N-dimethylformamide;
DMA N,N-dimethylacetamide;
DMSO dimethylsulfoxide;
dppf 1,1'-bis(diphenylphosphino)ferrocene
halogen means F, Cl, Br or J, preferably F, Cl or Br;
hemiacetal refers to the adduct of an alcohol, for instance methanol or ethanol, with a ketone or with an aldehyde; a hemiacetal may also result upon the addition of water to an enol ether; for instance, the hemiacetal of methanol with trifluoroacetone is $F_3C$—C(OH)(OCH$_3$)—CH$_3$;
hexanes mixture of isomeric hexanes;
hydrate refers to the adduct of water with a ketone or with an aldehyde, for instance, the hydrate of trifluoroacetone is $F_3C$—C(OH)$_2$—CH$_3$;
LDA Lithium diisopropyl amide
NMP N-methyl-2-pyrrolidone;
sulfamic acid HO—$SO_2$—$NH_2$;
THF tetrahydrofuran;
trifluoroacetone 1,1,1-trifluoropropan-2-one;
xylene 1,2-dimethylbenzene, 1,3-dimethylbenzene, 1,4-dimethylbenzene or a mixture thereof.

SUMMARY OF THE INVENTION

Subject of the invention is a method for preparation of compound of formula (I);

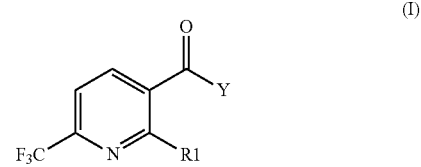

the method comprises a step (StepS1);
step (StepS1) comprises a reaction (ReacS1);
reaction (ReacS1) is a reaction of a compound of formula (II) with a compound of formula (III) and a compound of formula (IV);
compound of formula (II) is selected from the group consisting of compound of formula (II-1), compound of formula (II-2), compound of formula (IIa), and mixtures thereof;

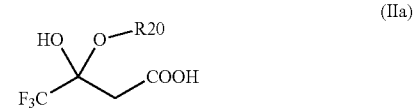

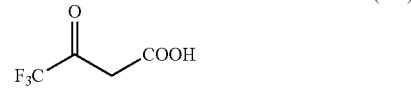

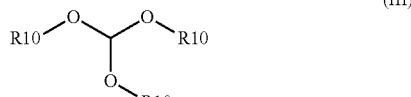

R1 is selected from the group consisting of $C_{1-10}$ alkyl, $C_{3-8}$ cycloalkyl, C(O)—O—$C_{1-4}$ alkyl, CH=$CH_2$, benzyl, phenyl and naphthyl;
the $C_{1-10}$ alkyl of R1 is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, S(O$_2$)—$C_{1-10}$ alkyl, O—$C_{1-6}$ alkylen-O—$C_{1-6}$ alkyl, $C_{3-8}$ cycloalkyl and 1,2,4-triazolyl;
the benzyl, the phenyl and the naphthyl of R1 are independently from each other unsubstituted or substituted with 1, 2, 3, 4 or 5 identical or different substituents selected from the group consisting of halogen, $C_{1-4}$ alkoxy, NO$_2$ and CN;
Y is selected from the group consisting of $C_{1-6}$ alkoxy, O—$C_{1-6}$ alkylen-O—$C_{1-6}$ alkyl, NH$_2$, NHR4 and N(R4)R5;
R4 and R5 are identical or different and independently from each other $C_{1-6}$ alkyl, or represent together a tetramethylene or a pentamethylene chain;

R10 is selected from the group consisting of $C_{1-8}$ alkyl, $C_{3-10}$ cycloalkyl and phenyl, said phenyl is unsubstituted or substituted with 1 or 2 identical or different substituents independently from each other selected from the group consisting of halogen, cyano, nitro, $C_{1-6}$ alkyl and phenyl;
R20 is selected from the group consisting of $C_{1-6}$ alkyl, $O(CO)CH_3$, $O(CO)CF_3$, and $OSO_3H$.

DETAILED DESCRIPTION OF THE INVENTION

Compound of formula (II), compound of formula (III) and compound of formula (IV) are simultaneously present in step (StepS1) and in reaction (ReacS1), therefore reaction (ReacS1) is preferably done in one pot, i.e. reaction (ReacS1) is a one pot reaction.

Preferably, R1 is selected from the group consisting of $C_{1-5}$ alkyl, $C_{3-6}$ cycloalkyl, $C(O)$—$O$—$C_{1-4}$ alkyl, $CH=CH_2$, benzyl and phenyl;

said $C_{1-5}$ alkyl of R1 is unsubstituted or substituted with 1, 2, 3, 4 or 5 identical of different substituents selected from the group consisting of halogen, OH, O—C(O)—CH$_3$, O—$C_{1-5}$ alkyl, S—$C_{1-5}$ alkyl, S(O)—$C_{1-5}$ alkyl, $S(O_2)$—$C_{1-5}$ alkyl, O—$C_{1-4}$ alkylen-O—$C_{1-4}$ alkyl, $C_{3-6}$ cycloalkyl and 1,2,4-triazolyl;

said benzyl and said phenyl of R1 are independently from each other unsubstituted or substituted with 1, 2, 3, 4 or 5 identical of different substituents selected from the group consisting of halogen, $C_{1-2}$ alkoxy, $NO_2$ and CN;

more preferably, R1 is selected from the group consisting of methyl, ethyl, isopropyl, tert-butyl, cyclopropyl, trifluoromethyl, difluoromethyl, chloromethyl, bromomethyl, C(O)—O—CH$_3$, C(O)—O—C$_2$H$_5$, CH$_2$—O—C(O)—CH$_3$, CH$_2$—O—CH$_3$, CH$_2$—S—CH$_3$, CH$_2$—S(O$_2$)—CH$_3$, CH$_2$—CH$_2$—O—CH$_3$, CH$_2$—O—CH$_2$—CH$_2$—O—CH$_3$, CH$_2$—O—CH$_2$—CH$_2$—O—CH$_2$—CH$_3$, CH=CH$_2$ and phenyl.

even more preferably, R1 is selected from the group consisting of methyl, ethyl, chloromethyl, bromomethyl, CH$_2$—O—C(O)—CH$_3$, and CH$_2$—O—CH$_2$—CH$_2$—O—CH$_3$;

especially, R1 is selected from the group consisting of methyl, chloromethyl, and CH$_2$—O—CH$_2$—CH$_2$—O—CH$_3$.

Preferably, Y is selected from the group consisting of $C_{1-6}$ alkoxy, NHR4 and N(R4)R5;

R4 and R5 are identical or different and independently from each other $C_{1-6}$ alkyl, or represent together a tetramethylene or a pentamethylene chain;

more preferably, Y is selected from the group consisting of methoxy and ethoxy.

Preferably, R10 is selected from the group consisting of $C_{1-8}$ alkyl, $C_{3-10}$ cycloalkyl and phenyl, said phenyl being unsubstituted or substituted with 1 or 2 identical or different substituents independently from each other selected from the group consisting of halogen, cyano, nitro, and $C_{1-6}$ alkyl;

more preferably, R10 is selected from the group consisting of $C_{1-8}$ alkyl, $C_{3-10}$ cycloalkyl and phenyl, said phenyl being unsubstituted or substituted with 1 or 2 identical or different substituents independently from each other selected from the group consisting of halogen and $C_{1-6}$ alkyl;

even more preferably, R10 is selected from the group consisting of $C_{1-6}$ alkyl, $C_{3-6}$ cycloalkyl and phenyl;

especially, R10 is selected from the group consisting of $C_{1-4}$ alkyl;

more especially, R10 is methyl or ethyl.

Preferably, R20 is selected from the group consisting of $C_{1-4}$ alkyl, $O(CO)CH_3$, $O(CO)CF_3$, and $OSO_3H$;

more preferably R20 is selected from the group consisting of methyl, ethyl, $O(CO)CH_3$, $O(CO)CF_3$, and $OSO_3H$;

even more preferably R2 is methyl or ethyl.

Preferably, compound of formula (II) is selected from the group consisting of compound of formula (II-1), compound of formula (II-2), and mixtures thereof.

Preferably, the molar ratio [compound of formula (II): compound of formula (III)] is from [1:0.9] to [1:100], more preferably from [1:0.9] to [1:10], even more preferably from [1:0.9] to [1:5], especially from [1:0.9] to [1:2.5].

Preferably, the molar ratio [compound of formula (II): compound of formula (IV)] is from [20:1] to [1:20], more preferably from [10:1] to [1:10], even more preferably from [10:1] to [1:5], especially from [10:1] to [1:3].

Reaction (ReacS1) can be done in a solvent;

preferably, the solvent is a solvent (SolvS1) and solvent (SolvS1) is preferably selected from the group consisting of ethyl acetate, butyl acetate, dichloromethane, chloroform, acetonitrile, propionitrile, DMF, DMA, DMSO, sulfolane, THF, 2-methyl-THF, 3-methyl-THF, dioxane, 1,2-dimethoxyethane, toluene, benzene, chlorobenzene, nitrobenzene, and mixtures thereof;

more preferably, solvent (SolvS1) is selected from the group consisting of ethyl acetate, butyl acetate, dichloromethane, acetonitrile, propionitrile, DMF, DMA, sulfolane, THF, 2-methyl-THF, 3-methyl-THF, dioxane, 1,2-dimethoxyethane, toluene, benzene, chlorobenzene, and mixtures thereof;

even more preferably, solvent (SolvS1) is selected from the group consisting of ethyl acetate, butyl acetate, dichloromethane, acetonitrile, DMF, DMA, dioxane, 1,2-dimethoxyethane, toluene, chlorobenzene, and mixtures thereof.

Preferably, the weight of solvent (SolvS1) is from 0.1 to 100 times, more preferably from 1 to 50 times, even more preferably from 1 to 25 times, of the weight of compound of formula (II).

Reaction (ReacS1) can be done in the presence of an acid, preferably the acid is a compound (AddS1);

compound (AddS1) is selected from the group consisting of acetic acid, propionic acid, trifluoroacetic acid, trichloroacetic acid, dichloroacetic acid, sulfuric acid, hydrochloric acid, acetic acid anhydride, acetyl chloride, toluenesulfonic acid, camphorsulfonic acid, methanesulfonic acid, and mixtures thereof preferably, compound (AddS1) is selected from the group consisting of acetic acid, propionic acid, trifluoroacetic acid, trichloroacetic acid, sulfuric acid, hydrochloric acid, acetic acid anhydride, toluenesulfonic acid, methanesulfonic acid, and mixtures thereof;

more preferably, compound (AddS1) is selected from the group consisting of acetic acid, trifluoroacetic acid, trichloroacetic acid, sulfuric acid, hydrochloric acid, acetic acid anhydride, methanesulfonic acid, and mixtures thereof;

even more preferably, compound (AddS1) is selected from the group consisting of acetic acid, trifluoroacetic acid, trichloroacetic acid, sulfuric acid, and mixtures thereof.

Preferably, the molar ratio [compound of formula (II): compound (AddS1)] is from [1:0.001] to [1:100], more preferably from [1:0.01] to [1:10], even more preferably from [1:0.05] to [1:5], especially [1:0.05] to [1:2], more especially [1:0.05] to [1:1], even more especially [1:0.05] to [1:0.5].

Preferably, the reaction temperature of reaction (ReacS1) is from −50 to 250° C., more preferably from −20 to 180° C., even more preferably from 0 to 150° C., especially from 10 to 150° C., more especially from 50 to 120° C.

Preferably, reaction (ReacS1) is done at a pressure of from ambient pressure to 20 bar, more preferably of from ambient pressure to 15 bar, even more preferably of from ambient pressure to 10 bar.

Preferably, the reaction time of reaction (ReacS1) is from 30 min to 96 h, more preferably from 45 min to 48 h, even more preferably from 45 min to 36 h, especially from 45 min to 24 h, more especially from 1 h to 24 h.

After reaction (ReacS1), compound of formula (I) can be isolated by any conventional method.

Preferably, compound of formula (I) is isolated after reaction (ReacS1) by hydrolysis and acidification of the reaction mixture resulting from reaction (ReacS1).

Hydrolysis and acidification is preferably done by addition of a compound (InAcS1), compound (InAcS1) is an aqueous inorganic acid, preferably compound (InAcS1) is selected from the group consisting of aqueous hydrochloric acid and aqueous sulfuric acid.

After hydrolysis and acidification, any solvent (SolvS1) is preferably removed by distillation; compound of formula (I) is preferably extracted by extraction with a solvent (SolvExtrS1), solvent (SolvExtrS1) is preferably selected from the group consisting of ethyl acetate, isopropyl acetate, butyl acetate, toluene, chlorobenzene, dichloromethane, chloroform and mixtures thereof the extraction is preferably followed by removal of solvent (SolvExtrS1) by distillation.

Also possible is the purification of compound of formula (I) by saponification by treatment of the reaction mixture resulting from reaction (ReacS1) or by treatment of the crude product of formula (I) with an aqueous or methanolic solution of NaOH or KOH, followed by acidification and extraction with solvent (SolvExtrS1), preferably followed by removal of solvent (SolvExtrS1) by distillation, to yield compound of formula (I) with Y=OH.

Compounds of formula (II) are known compounds and can be prepared by or in analogy of known methods.

For instance compound of formula (II-2) can be prepared by saponification of ethyl trifluoroacetoacetate as taught by F. Swarts, Bulletin de la Classe des Sciences, Academie Royale de Belgique, 1926, 12, 721-725.

Compound of formula (III) is commercially available or can be prepared by in analogy of known methods.

Compounds of formula (IV) are known compounds and can be prepared by or in analogy of known methods, for instance as described in WO 2004/078729 A1.

Further subject of the invention is the use of compound of formula (I) for the preparation of pharmaceutical, chemical or agro-chemical products,
with compound of formula (I) as defined above, also with all their preferred embodiments,
wherein compound of formula (I) has been prepared according to the method as described above, also with all their preferred respective embodiments.

EXAMPLES

Example 1

Reaction (ReacS1)

A mixture of compound of formula (II-2) (0.10 g, 0.64 mmol), DMF (0.5 ml), compound of formula (IV-1) (74 mg, 0.64 mmol), compound of formula (III-1) (0.16 ml, 0.96 mmol),

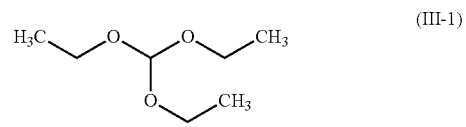

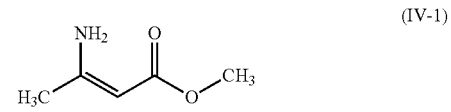

and sulfuric acid (0.007 ml, 0.13 mmol) was stirred at 80° C. for 3 h. A sample of the reaction mixture was diluted with brine (3 ml) and aqueous hydrochloric acid (1 N, 2 ml), and extracted with ethyl acetate (3 ml). After concentration under reduced pressure of the extract the analysis by $^1$H NMR showed compound of formula (I-1).

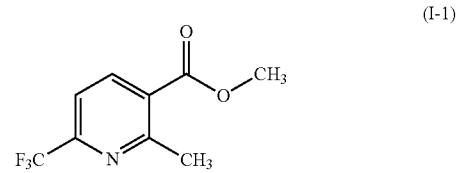

$^1$H NMR (400 MHz, $d_6$-DMSO): delta 2.78 (s, 3H), 3.91 (s, 3H), 7.89 (d, J=8 Hz, 1H), 8.44 (d, J=8 Hz, 1H).

Example 2

Reaction (ReacS1)

A mixture of compound of formula (II-2) (0.12 g, 0.77 mmol), toluene (0.5 ml), compound of formula (IV-1) (113 mg, 0.98 mmol), compound of formula (III-1) (0.16 ml, 0.96 mmol), and trifluoroacetic acid (0.01 ml, 0.13 mmol) was stirred at 80° C. for 17 h. A sample of the reaction mixture was diluted with brine (3 ml) and aqueous hydrochloric acid (1 N, 2 ml), and extracted with ethyl acetate (3 ml). After concentration of the extract under reduced pressure the analysis by $^1$H NMR showed compound of formula (I-1), $^1$H NMR data was as shown in example 1.

Example 3

Reaction (ReacS1)

A mixture of compound of formula (II-2) (0.169 g, 1.08 mmol), toluene (0.52 ml), compound of formula (IV-2) (0.26 mmol, prepared in analogy to example P2 of WO 2004/078729 A1, wherein the reaction mixture, which is obtained after cooling and which contains 3-amino-4-methoxyethoxy-but-2-enoic acid ethyl ester, which is compound of formula (IV-2), is taken and concentrated under reduced pressure, the thus obtained residue was used in instant example, the content of compound of formula (IV-2) in this residue is determined by $^1$H-NMR against a standard),

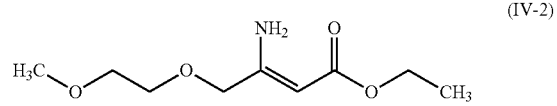

compound of formula (III-1) (0.40 ml, 2.4 mmol), and trifluoroacetic acid (0.01 ml, 0.13 mmol) was stirred at 80° C. for 18 h. The mixture was diluted with aqueous hydrochloric acid (1 N, 10 ml), extracted with ethyl acetate (1 time with 5 ml, 2 times with 2.5 ml), the combined extracts were washed with brine (5 ml), dried (MgSO$_4$), and concentrated under reduced pressure, to yield the compound of formula (I-2) as an oil (114 mg).

Quantification by $^1$H NMR with an internal standard (4-nitrobenzaldehyde) indicated, that the yield with respect to compound of formula (IV) was 54%.

$^1$H NMR (400 MHz, CDCl$_3$): delta 1.42 (t, J=7 Hz, 3H), 3.36 (s, 3H), 3.57 (m, 2H), 3.71 (m, 2H), 4.43 (q, J=7 Hz, 2H), 5.02 (s, 2H), 7.68 (d, J=8 Hz, 1H), 8.26 (d, J=8 Hz, 1H).

The invention claimed is:

1. A method for the preparation of a compound of formula (I);

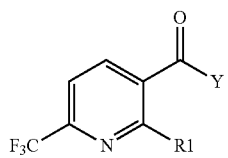

the method comprises a step (StepS1);
step (StepS1) comprises a reaction (ReacS1);
reaction (ReacS1) is a reaction of a compound of formula (II) with a compound of formula (III) and a compound of formula (IV);
the compound of formula (II) is selected from the group consisting of a compound of formula (II-1), a compound of formula (II-2), a compound of formula (IIa), and mixtures thereof;

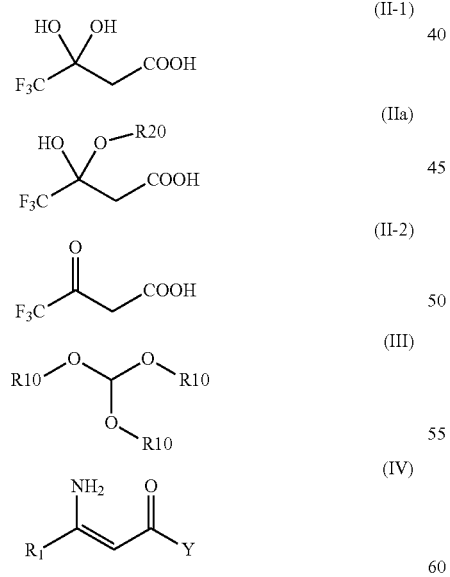

R1 is selected from the group consisting of C$_{1-10}$ alkyl, C$_{3-8}$ cycloalkyl, C(O)—O—C$_{1-4}$ alkyl, CH=CH$_2$, benzyl, phenyl and naphthyl;
the C$_{1-10}$ alkyl of R1 is unsubstituted or substituted with 1, 2, 3, 4 or 5 identical or different substituents selected from the group consisting of halogen, OH, O—C(O)—C$_{1-5}$ alkyl, O—C$_{1-10}$ alkyl, S—C$_{1-10}$ alkyl, S(O)—C$_{1-10}$ alkyl, S(O$_2$)—C$_{1-10}$ alkyl, O—C$_{1-6}$ alkylen-O—C$_{1-6}$ alkyl, C$_{3-8}$ cycloalkyl and 1,2,4-triazolyl;
the benzyl, the phenyl and the naphthyl of R1 are independently from each other unsubstituted or substituted with 1, 2, 3, 4 or 5 identical or different substituents selected from the group consisting of halogen, C$_{1-4}$ alkoxy, NO$_2$ and CN;
Y is selected from the group consisting of C$_{1-6}$ alkoxy, O—C$_{1-6}$ alkylen-O—C$_{1-6}$ alkyl, NH$_2$, NHR4 and N(R4)R5;
R4 and R5 are identical or different and independently from each other C$_{1-6}$ alkyl, or represent together a tetramethylene or a pentamethylene chain;
R10 is selected from the group consisting of C$_{1-8}$ alkyl, C$_{3-10}$ cycloalkyl and phenyl, said phenyl is unsubstituted or substituted with 1 or 2 identical or different substituents independently from each other selected from the group consisting of halogen, cyano, nitro, C$_{1-6}$ alkyl and phenyl;
R20 is selected from the group consisting of C$_{1-6}$ alkyl, O(CO)CH$_3$, O(CO)CF$_3$, and OSO$_3$H.

2. The method according to claim 1, wherein reaction (ReacS1) is done in one pot.

3. The method according to claim 1, wherein
R1 is selected from the group consisting of C$_{1-5}$ alkyl, C$_{3-6}$ cycloalkyl, C(O)—O—C$_{1-4}$ alkyl, CH=CH$_2$, benzyl and phenyl;
said C$_{1-5}$ alkyl of R1 is unsubstituted or substituted with 1, 2, 3, 4 or 5 identical of different substituents selected from the group consisting of halogen, OH, O—C(O)—CH$_3$, O—C$_{1-5}$ alkyl, S—C$_{1-5}$ alkyl, S(O)—C$_{1-5}$ alkyl, S(O$_2$)—C$_{1-5}$ alkyl, O—C$_{1-4}$ alkylen-O—C$_{1-4}$ alkyl, C$_{3-6}$ cycloalkyl and 1,2,4-triazolyl;
said benzyl and said phenyl of R1 are independently from each other unsubstituted or substituted with 1, 2, 3, 4 or 5 identical of different substituents selected from the group consisting of halogen, C$_{1-2}$ alkoxy, NO$_2$ and CN.

4. The method according to claim 1, wherein
Y is selected from the group consisting of C$_{1-6}$ alkoxy, NHR4 and N(R4)R5;
R4 and R5 are identical or different and independently from each other C$_{1-6}$ alkyl, or represent together a tetramethylene or a pentamethylene chain;

5. The method according to claim 1, wherein
R10 is selected from the group consisting of C$_{1-8}$ alkyl, C$_{3-10}$ cycloalkyl and phenyl,
said phenyl being unsubstituted or substituted with 1 or 2 identical or different substituents independently from each other selected from the group consisting of halogen, cyano, nitro, and C$_{1-6}$ alkyl.

6. The method according to claim 1, wherein
R20 is selected from the group consisting of C$_{1-4}$ alkyl, O(CO)CH$_3$, O(CO)CF$_3$, and OSO$_3$H.

7. The method according to claim 1, wherein
the compound of formula (II) is selected from the group consisting of the compound of formula (II-1), the compound of formula (II-2), and mixtures thereof.

8. The method according to claim 1, wherein
reaction (ReacS1) is done in a solvent;
the solvent is a solvent (SolvS1) and the solvent (SolvS1) is selected from the group consisting of ethyl acetate, butyl acetate, dichloromethane, chloroform, acetonitrile, propionitrile, DMF, DMA, DMSO, sulfolane, THF, 2-methyl-THF, 3-methyl-THF, dioxane, 1,2-dimethoxyethane, toluene, benzene, chlorobenzene, nitrobenzene, and mixtures thereof.

9. The method according to claim 1, wherein
reaction (ReacS1) is done in the presence of an acid, the acid is a compound (AddS1);
the compound (AddS1) is selected from the group consisting of acetic acid, propionic acid, trifluoroacetic acid, trichloroacetic acid, dichloroacetic acid, sulfuric acid, hydrochloric acid, acetic acid anhydride, acetyl chloride, toluenesulfonic acid, camphorsulfonic acid, methanesulfonic acid, and mixtures thereof.

* * * * *